(12) United States Patent
Lee et al.

(10) Patent No.: US 8,431,763 B2
(45) Date of Patent: *Apr. 30, 2013

(54) SEPARATION METHOD OF AROMATIC COMPOUNDS COMPRISING SIMULATED MOVING BED XYLENE MIXTURE PRE-TREATMENT PROCESS AND ADDITIONAL XYLENE ISOMERIZATION PROCESS

(75) Inventors: Jin-Suk Lee, Seoul (KR); Hyun-Chul Kim, Seosan-si (KR)

(73) Assignee: Samsung Total Petrochemicals Co., Ltd., Chungcheongnam-do (KR)

( * ) Notice: Subject to any disclaimer, the term of this patent is extended or adjusted under 35 U.S.C. 154(b) by 283 days.

This patent is subject to a terminal disclaimer.

(21) Appl. No.: 12/532,751

(22) PCT Filed: Oct. 31, 2007

(86) PCT No.: PCT/KR2007/005470
§ 371 (c)(1),
(2), (4) Date: Dec. 29, 2009

(87) PCT Pub. No.: WO2008/133384
PCT Pub. Date: Nov. 6, 2008

(65) Prior Publication Data
US 2010/0145119 A1  Jun. 10, 2010

(30) Foreign Application Priority Data

Apr. 27, 2007 (KR) .......................... 10-2007-0041569

(51) Int. Cl.
*C07C 7/14* (2006.01)
(52) U.S. Cl.
USPC ........... 585/814; 585/821; 585/831; 585/815; 585/479

(58) Field of Classification Search ........................ None
See application file for complete search history.

(56) References Cited

U.S. PATENT DOCUMENTS

| | | |
|---|---|---|
| 5,284,992 A | 2/1994 | Hotier et al. |
| 5,329,060 A | 7/1994 | Swift |
| 5,401,476 A | 3/1995 | Hotier et al. |
| 5,629,467 A | 5/1997 | Hotier et al. |
| 5,866,740 A | 2/1999 | Mikitenko et al. |
| 5,922,924 A | 7/1999 | Hotier et al. |
| 5,948,950 A | 9/1999 | Hotier et al. |
| 6,004,452 A | 12/1999 | Ash et al. |
| 6,063,978 A | 5/2000 | Hotier et al. |
| 6,281,406 B1 | 8/2001 | Cain |

(Continued)

OTHER PUBLICATIONS

International search report dated Jan. 22, 2008 in corresponding PCT/KR2007/005470.

*Primary Examiner* — Tam M Nguyen
(74) *Attorney, Agent, or Firm* — Young & Thompson

(57) ABSTRACT

Disclosed is a method for separating aromatic compounds using a simulated moving bed adsorptive chromatography, comprising a sulfolan process that is a non-aromatic compound removing process, a benzene/toluene fractionation process, an aromatic compound fractionation process, a selective toluene disproportionation process, a transalkylation process, a simulated moving bed para-xylene separation process and a xylene isomerization process, wherein the method is characterized by further comprising a simulated moving bed xylene mixture pre-treatment process and an additional xylene isomerization process. The separation method of aromatic compounds according to the present invention can make significant improvement in para-xylene and benzene production in the overall process, as compared to the conventional aromatic compound separation process.

9 Claims, 3 Drawing Sheets

U.S. PATENT DOCUMENTS

| | | |
|---|---|---|
| 6,342,649 B1 | 1/2002 | Winter et al. |
| 6,359,186 B1 * | 3/2002 | Hotier et al. .................. 585/820 |
| 6,376,734 B1 | 4/2002 | Magne-Drisch et al. |
| 6,774,273 B2 | 8/2004 | Xie et al. |
| 6,841,714 B2 | 1/2005 | Leflaive et al. |
| 2007/0149841 A1 * | 6/2007 | Lee et al. ...................... 585/826 |

* cited by examiner

SEPARATION METHOD OF AROMATIC COMPOUNDS COMPRISING SIMULATED MOVING BED XYLENE MIXTURE PRE-TREATMENT PROCESS AND ADDITIONAL XYLENE ISOMERIZATION PROCESS

TECHNICAL FIELD

The present invention relates to a method for separating aromatic compounds comprising a simulated bed xylene mixture pre-treatment process and an additional xylene isomerization process, specifically to a method for separating aromatic compounds using a simulated moving bed adsorptive chromatography, comprising a sulfolan process that is a non-aromatic compound removing process, a benzene/toluene fractionation process, an aromatic compound fractionation process, a selective toluene disproportionation process, a transalkylation process, a simulated moving bed para-xylene separation process and a xylene isomerization process, wherein the method is characterized by further comprising a simulated moving bed xylene mixture pre-treatment process and an additional xylene isomerization process.

BACKGROUND ART

A process of separating aromatic compounds is to obtain para-xylene and benzene as main final products by processing a naphtha feedstock in a petrochemical plant. To obtain para-xylene, one of important products among aromatic compounds, a process of separating it from a xylene mixture has been commonly used. As examples of such process, there are processes using simulated moving bed adsorptive chromatography and crystallization caused by freezing point difference in each component, or a hybrid process which uses both processes together by connecting them serially, and the like.

DISCLOSURE OF INVENTION

Technical Problem

In a process of separating aromatic compounds using a conventional simulated moving bed adsorptive chromatography as shown in FIG. 1, the simulated moving bed para-xylene separation process is only used as a process for separating para-xylene. Such process has some problems that there is limitation on increasing reformate production by inputting additional naphtha, and on enhancing productivity of para-xylene by further adding toluene, due to the limited capacity of a simulated moving bed para-xylene separation process, and it is further required to improve productivity in terms of para-xylene production since the excess xylene mixture which could not be processed in the simulated moving bed para-xylene separation process should be discharged.

Technical Solution

The present invention has been developed to resolve the conventional technical problems in prior arts. The object of the present invention is to provide a method for separating aromatic compounds using a simulated bed adsorptive chromatography, which can increase para-xylene concentration, hence being able to separate para-xylene in efficient way and effectively converting the excess xylene mixture into para-xylene by pretreating a xylene mixture through a simulated moving bed xylene mixture pre-treatment process and an additional xylene isomerization process; and can significantly improve the overall productivity of para-xylene and toluene by inputting a separate toluene mixture as well as a xylene mixture.

In order to achieve the forgoing purposes, the method for separating aromatic compounds according to the present invention, which uses a simulated moving bed adsorptive chromatography, comprising a sulfolan process that is a non-aromatic compound removing process, a benzene/toluene fractionation process, an aromatic compound fractionation process, a selective toluene disproportionation process, a transalkylation process, a simulated moving bed para-xylene separation process and a xylene isomerization process, is characterized by further comprising a simulated moving bed xylene mixture pre-treatment process and an additional xylene isomerization process.

The xylene mixture pre-treatment process and the additional xylene isomerization process preferably comprise the following steps of:

(1) inputting a part of a xylene mixture that is to be inputted to a simulated moving bed para-xylene separation process, to the simulated moving bed xylene mixture pre-treatment process;

(2) inputting a xylene mixture containing 80% by weight or more para-xylene in the resulted product obtained from said simulated moving bed xylene mixture pre-treatment process, to the simulated moving bed para-xylene separation process, and the remaining portion of the xylene mixture is inputted to the additional xylene isomerization process;

(3) re-inputting the resulted product obtained from said additional xylene isomerization process to said aromatic compound fractionation process.

In the step (1), the amount of a xylene mixture to be inputted to a simulated moving bed xylene mixture pre-treatment process is not specifically limited, and it may be suitably adjusted depending on the system conditions, however, preferably being 50~200 tons/hour.

In the step (3), a part of the product obtained from an additional xylene isomerization process, which is to be inputted to an aromatic compound fractionation process, may be inputted to a benzene/toluene fractionation process. The amount thereof to be inputted is not specifically limited, and it may be suitably adjusted depending on the system conditions, however, preferably being 1~10 tons/hour.

In the method for separating aromatic compounds, overall productivity of para-xylene may be improved, by additionally inputting toluene to a selective disproportionation process. Further, in the method for separating aromatic compounds, a xylene mixture can be additionally inputted to said aromatic compound fractionation process so as to improve overall productivity of para-xylene. Each amount of separate toluene and the separate xylene mixture to be inputted is not specifically limited, and it may be suitably adjusted depending on the system conditions, however preferably being 0~60 tons/hour and 0~30 tons/hour, respectively.

Hereinafter, the method for separating aromatic compounds of the present invention is further described in detail by referencing FIG. 2.

Reformate that is a mixture of aromatic compound feedstocks inputted from a reformer into a splitter (RS) is separated into a mixture containing aromatic compounds having 6 carbon atoms such as benzene and aromatic compounds having 7 carbon atoms such as toluene, and a mixture containing relatively heavy aromatic compounds such as xylene having 8 carbon atoms. The former is inputted to a sulfolan process (Sulfolane) that is to remove non-aromatics, and a benzene/toluene fractionation process(B/T Frac) through line(4), and the latter is inputted to an aromatic compound fractionation process(Aro Frac) through line(24).

In the benzene/toluene fractionation process, a mixture of benzene and toluene is separated to benzene and toluene, respectively, wherein benzene is discharged through line(12), and toluene is inputted to a selective toluene disproportionation process(STDP) and transalkylation process(TAC9) through line(14). The mixture resulted from a selective disproportionation reaction in the selective toluene disproportionation process contains benzene(A6), toluene(A7), xylene (A8), trimethylbenzene(A9) and the like, and particularly it contains para-xylene at the amount of about 85~95% by weight. The mixture is re-inputted to the benzene-toluene fractionation process through line(19), in which xylene having 8 carbon atoms and trimethylbenzene that is heavier than xylene are separated from the relatively light components, discharged through line(13), and inputted to an aromatic compound fractionation process through line(2).

In the aromatic compound fractionation process, aromatic compounds having 10 or more carbon atoms are discharged through line(3), and a xylene mixture is discharged through line(6) and input to the simulated moving bed para-xylene separation process(Parex). A part of the xylene mixture is inputted to a simulated moving bed xylene mixture pre-treatment process(New SMB). The xylene mixture inputted to the simulated moving bed xylene mixture pre-treatment process through line(35) is separated to a xylene mixture at high concentration having 80 wt % or more of para-xylene, and the residual xylene mixture. The former is directed to a simulated moving bed para-xylene separation process through line(36) and line(37), and the latter is inputted to an additional xylene isomerization process(ISOMAR2) through line(38). The products resulted from the additional xylene isomerization process is transferred via line(39) to desired processes; a portion is re-inputted to the aromatic compound fractionation process through line(39-1), and the other portion is inputted to a benzene/toluene fractionation process through line(39-2).

The xylene mixture inputted to the simulated moving bed para-xylene separation process through line(8) is separated to para-xylene and the residual xylene mixture. The former is discharged through line(9), and the latter is inputted to a xylene isomerization process(ISOMAR) through line(10). The product resulted from the xylene isomerization process is re-inputted to the aromatic compound fractionation process through line(11).

The aromatic compounds having 9 carbon atoms(A9) discharged from the aromatic compound fractionation process are inputted to a transalkylation process(TAC9) through line (20). Aromatic compounds having 9 carbon atoms inputted to the transalkylation process undergoes transalkylation with toluene inputted through line(18) from the benzene/toluene separation process, thus producing a resulted mixture containing para-xylene. The resulted mixture is re-inputted to the aromatic compound fractionation process through line(21).

Additional toluene is inputted to the line(14) via line(42), and the additional toluene mixture is inputted to the line (2) via line(43).

DEFINITIONS

Figure 1:
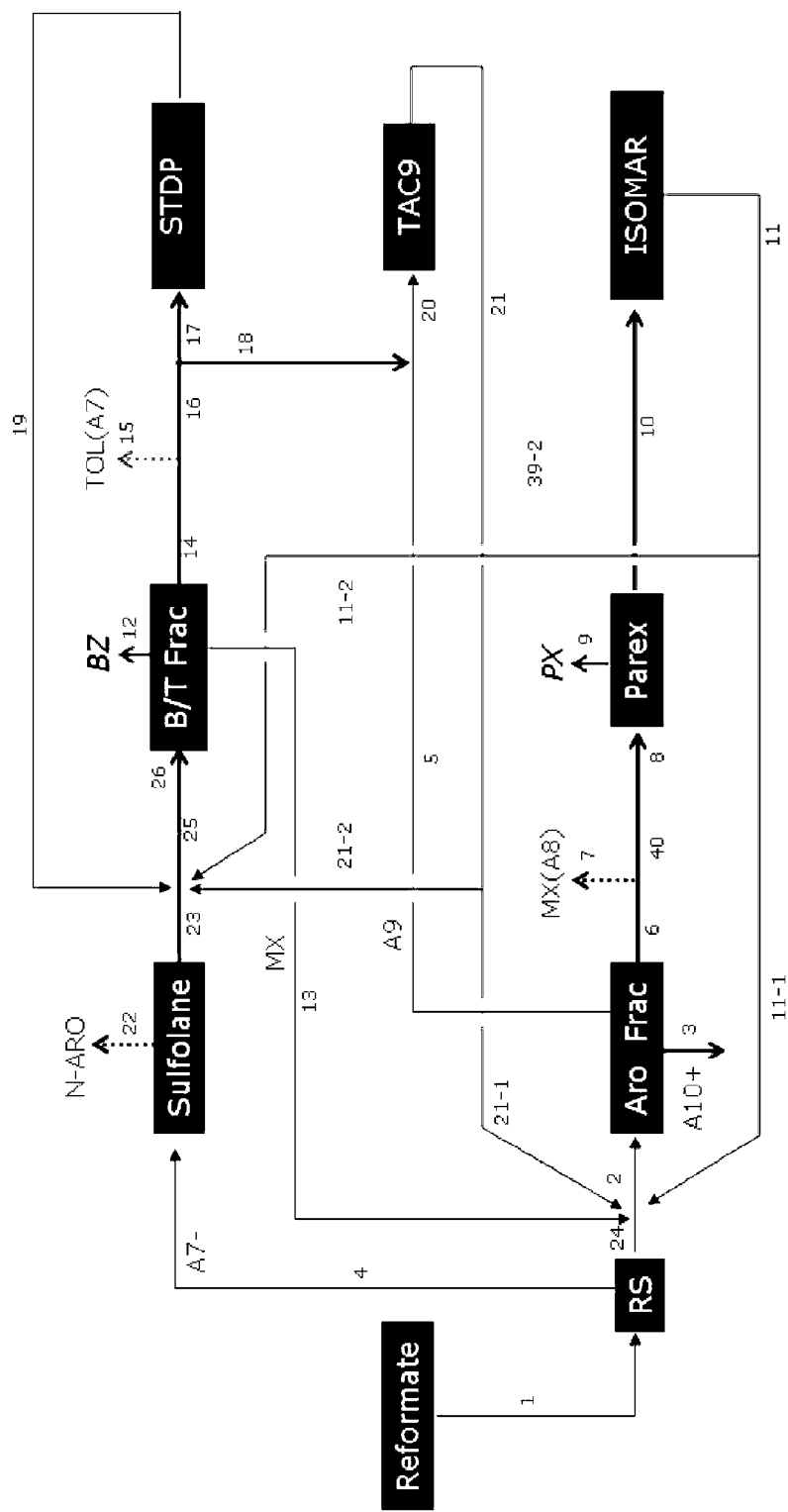
FIG. 1 is a schematic view of a conventional process of separating aromatic compounds using simulated moving bed adsorptive chromatography.

Sulfolane: a process of benzene/toluene fractionation and a process of removing non-aromatic compounds
Parex: a simulated moving bed para-xylene separation process
ISOMAR: a xylene isomerization process
ISOMAR2: an additional xylene isomerization process
STDP: a selective toluene disproportionation process
TAC9: a transalkylation process of aromatic compounds having 9 carbon atoms
B/T Frac: a benzene/toluene fractionation process
Aro Frac: an aromatic compound fractionation process
New SMB: a simulated moving bed xylene mixture pre-treatment process
A6: aromatic compounds having 6 carbon atoms
A7: aromatic compounds having 7 carbon atoms
A8: aromatic compounds having 8 carbon atoms
A9: aromatic compounds having 9 carbon atoms
A10+: aromatic compounds having 10 or more carbon atoms
BZ: benzene
PX: para-xylene
MX: xylene mixture
TOL: toluene

MODE FOR THE INVENTION

The present invention will be further specified through the following examples, which are described with only illustrative purpose, and by no means intended to limiting or restricting the scope of the present invention.

EXAMPLES OF THE INVENTION

Example

Figure 2:
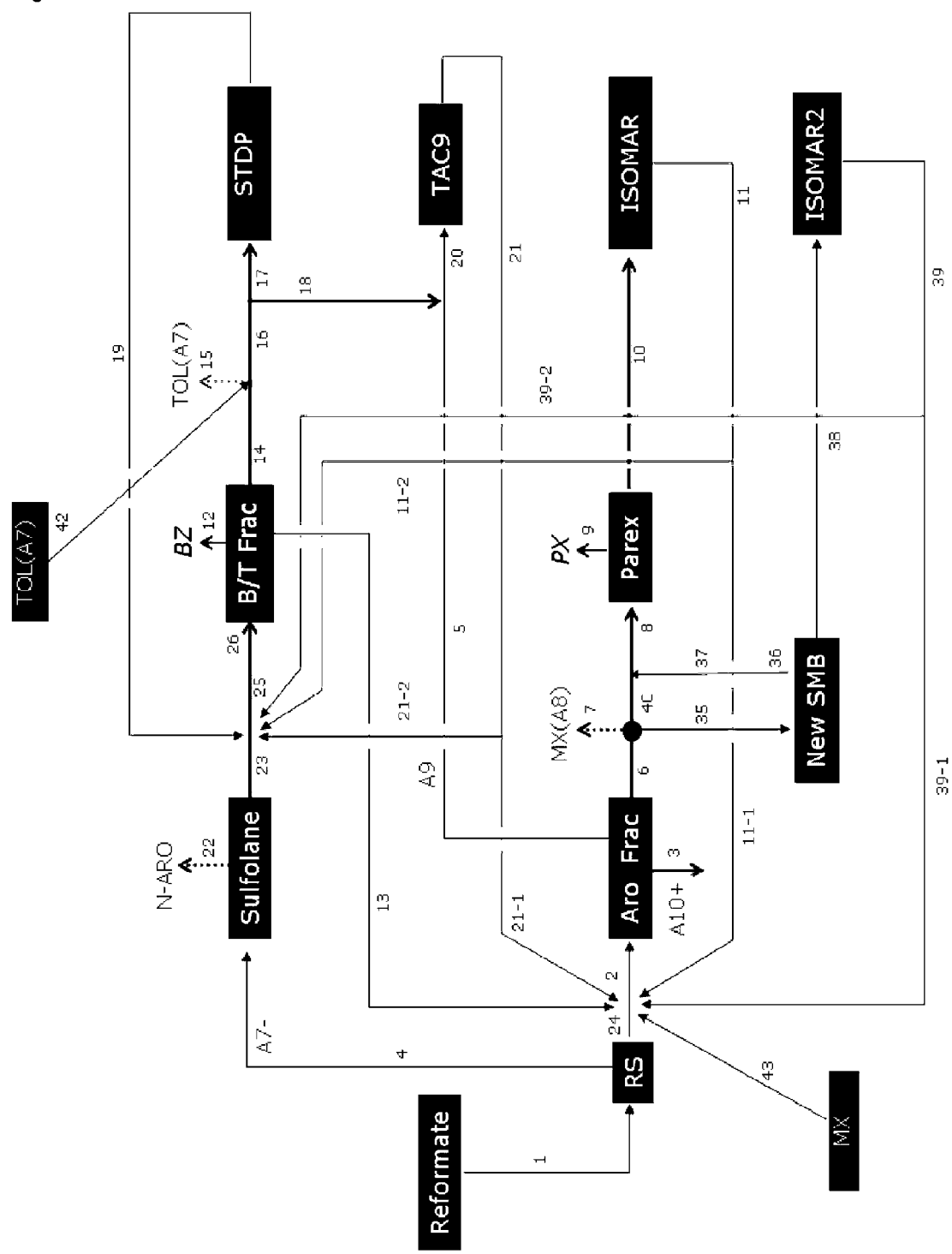
FIG. 2 is a schematic view of a process of separating aromatic compounds comprising a xylene mixture pre-treatment process and an additional xylene isomerization process according to the present invention.
Figure 3:
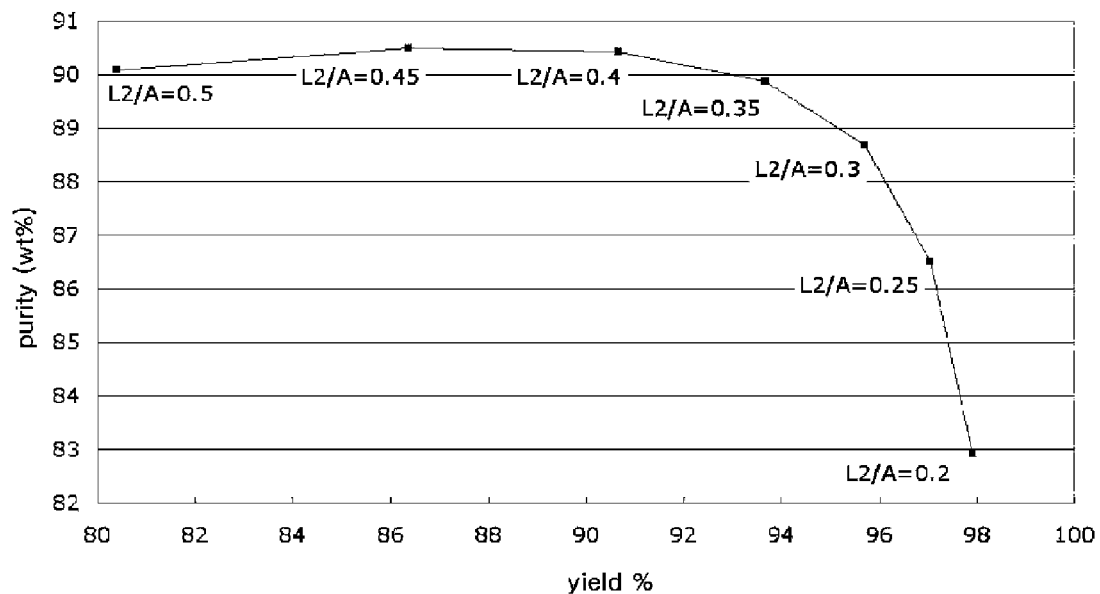
FIG. 3 is a graph showing the operation potential of a simulated moving bed xylene mixture pre-treatment process in 8 beds, which can maintain the concentration of para-xylene in an extract at 80% by weight or more by suitably adjusting the operation conditions.
Figure 4:
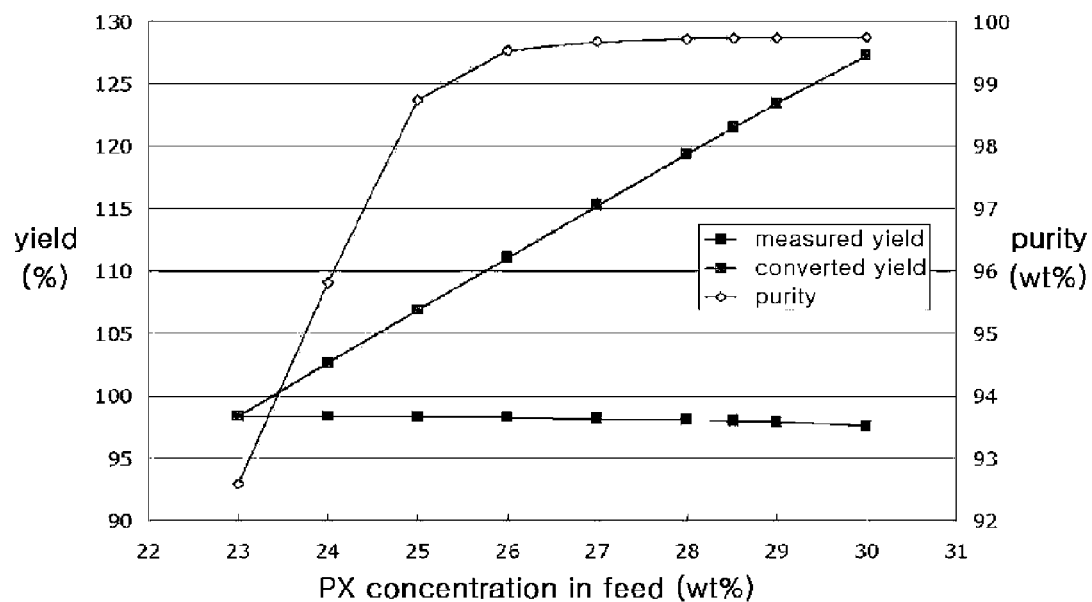
FIG. 4 is a graph showing the change of productivity represented as a change of converted yield as a function of a change in para-xylene concentration in a xylene mixture inputted into a simulated moving bed para-xylene separation process which is to separate para-xyelene. The converted yield may have a value of more than 100% because it was calculated on the base of 23% of para-xylene concentration in a xylene mixture.

The continuous production of para-xylene and benzene from naphtha using an aromatic compound separation process represented in FIG. 2 was computer-simulated.

Comparative Example

The production as in the Example was computer simulated in the same way, except that an aromatic compound separation process represented in FIG. 1 was used.

The feed amount to the simulated moving bed para-xylene process in the above Example was limited to 262 tons/hour or less that is an identical level with that of the Comparative example and the feed amount to the simulated moving bed xylene mixture pre-treatment process was limited to 150 tons/ hour or less. Such limitation is only to illustrate the present invention, however, by no means limiting or restricting the scope of the present invention sought to be protected.

Table 1 shows the results of the Example wherein a separate toluene was additionally input, and the Comparative example: the amount of naphtha feedstock consumed during the production period; the intermediately produced amount of reformate; each amount of para-xylene and benzene produced; and the para-xylene concentration in the feed to the simulated moving bed para-xylene separation process.

TABLE 1

|  | Example | Comparative example |
|---|---|---|
| Naphtha feedstock consumption(ton/hour) | 353.0 | 353.0 |
| Reformate production (ton/hour) | 176.0 | 176.0 |
| Toluene input (ton/hour) | 45.0 | 0.0 |
| Xylene mixture input (ton/hour) | 0.0 | 0.0 |
| Para-xylene production (ton/hour) | 103.4 | 70.6 |
| Benzene production (ton/hour) | 73.8 | 49.3 |
| Excess xylene mixture (ton/hour) | 0.0 | 7.0 |
| Excess toluene (ton/hour) | 0.0 | 5.3 |
| Feed rate to Parex process (ton/hour) | 261.2 | 261.5 |
| Para-xylene concentration in the feed to Parex process | 40.8 wt % | 27.8 wt % |

Reviewing the results shown in Table 1, the para-xylene concentration in the feed to the simulated moving bed para-xylene separation process in the Example according to the present invention was significantly improved as compared to the Comparative example, and each amount of para-xylene and benzene produced from the process during the same period was increased by 32.8 tons/hour and 24.5 tons/hour, respectively, as compared to the comparative example. When it is calculated as production in one year, it can be found that production increment of 287,000 tons and 215,000 tons may be obtained, respectively.

Table 2 shows the results of the Example wherein a separate xylene mixture was additionally input, and the Comparative example: the amount of naphtha feedstock consumed during the production period; the intermediately produced amount of reformate; each amount of para-xylene and benzene produced; and the para-xylene concentration in the feed to the simulated moving bed para-xylene separation process.

TABLE 2

|  | Example | Comparative example |
|---|---|---|
| Naphtha feedstock consumption(ton/hour) | 353.0 | 353.0 |
| Reformate production(ton/hour) | 176.0 | 176.0 |
| Toluene input(ton/hour) | 0.0 | 0.0 |
| Xylene mixture input (ton/hour) | 18.0 | 0.0 |
| Para-xylene production (ton/hour) | 95.0 | 70.6 |
| Benzene production (ton/hour) | 55.3 | 49.3 |
| Excess xylene mixture (ton/hour) | 0.0 | 7.0 |
| Excess toluene (ton/hour) | 0.0 | 5.3 |
| Feed rate to Parex process (ton/hour) | 261.5 | 261.5 |
| Para-xylene concentration in the feed to Parex process | 37.4 wt % | 27.8 wt % |

Reviewing the results shown in Table 2, the para-xylene concentration in the feed to the simulated moving bed para-xylene separation process in the Example according to the present invention was significantly improved as compared to the Comparative example, and each amount of para-xylene and benzene produced from the process during the same period was increased by 24.4 tons/hour and 6 tons/hour, respectively, as compared to the Comparative example. When it is calculated as production in one year, it can be found that production increment of 214,000 tons and 53,000 tons may be obtained, respectively.

Table 3 shows the results of the Example wherein a separate toluene and a xylene mixture were additionally input together, and the Comparative example: the amount of naphtha feedstock consumed during the production period; the intermediately produced amount of reformate; each amount of para-xylene and benzene produced; and the para-xylene concentration in the feed to the simulated moving bed para-xylene separation process.

TABLE 3

|  | Example | Comparative example |
|---|---|---|
| Naphtha feedstock consumption(ton/hour) | 353.0 | 353.0 |
| Reformate production(ton/hour) | 176.0 | 176.0 |
| Toluene input(ton/hour) | 20.0 | 0.0 |
| Xylene mixture input (ton/hour) | 10.0 | 0.0 |
| Para-xylene production (ton/hour) | 98.7 | 70.6 |
| Benzene production (ton/hour) | 63.5 | 49.3 |
| Excess xylene mixture(ton/hour) | 0.0 | 7.0 |
| Excess toluene (ton/hour) | 0.0 | 5.3 |
| Feed rate to Parex process (ton/hour) | 261.2 | 261.5 |
| Para-xylene concentration in the feed to Parex process | 39.0 wt % | 27.8 wt % |

Reviewing the results shown in Table 3, the para-xylene concentration in the feed to the simulated moving bed para-xylene separation process in the Example according to the present invention was significantly improved as compared to the Comparative example, and amount of each para-xylene and benzene produced from the process during the same period was increased by 28.1 tons/hour and 14.2 tons/hour, respectively, as compared to the Comparative example. When it is calculated as production in one year, it can be found that production increment of 246,000 tons and 124,000 tons may be obtained, respectively.

Table 4 shows the results of the Example wherein an increased amount of reformate was input, and the Comparative example: the amount of naphtha feedstock consumed during the production period; the intermediately produced amount of reformate; each amount of para-xylene and benzene produced; and the para-xylene concentration in the feed to the simulated moving bed para-xylene separation process.

TABLE 4

|  | Example | Comparative example |
|---|---|---|
| Naphtha feedstock consumption(ton/hour) | 429.0 | 353.0 |
| Reformate production(ton/hour) | 214.0 | 176.0 |
| Toluene input(ton/hour) | 0.0 | 0.0 |
| Xylene mixture input (ton/hour) | 0.0 | 0.0 |
| Para-xylene production (ton/hour) | 96.5 | 70.6 |
| Benzene production (ton/hour) | 64.2 | 49.3 |
| Excess xylene mixture(ton/hour) | 0.0 | 7.0 |
| Excess toluene (ton/hour) | 0.0 | 5.3 |
| Feed rate to Parex process (ton/hour) | 260.8 | 261.5 |
| Para-xylene concentration in the feed to Parex process | 38.2 wt % | 27.8 wt % |

From the results shown in Table 4, it can be found that the para-xylene concentration in the feed to the simulated moving bed para-xylene separation process in the Example of the present invention was significantly improved as compared to the Comparative example; and each amount of para-xylene and benzene produced from the process during the same period was increased by 25.9 tons/hour and 14.9 tons/hour, respectively, as compared to the Comparative example. When it is calculated as production in one year, it can be found that production increment of 227,000 tons and 131,000 tons may be obtained, respectively.

INDUSTRIAL APPLICABILITY

As it has been described so far, the separation method of aromatic compounds according to the present invention can make significant improvement in para-xylene and benzene production in the overall process, as compared to the conventional aromatic compound separation process.

The invention claimed is:

1. A method for separating aromatic compounds using a simulated moving bed adsorptive chromatography, comprising:
    removing a non-aromatic compound from a mixture of aromatic compounds having 7 or less carbon atoms in a sulfolan step;
    fractionating benzene/toluene;
    fractionating an aromatic compound which separates aromatic compounds having 8 or more carbon atoms;
    selectively disproportionating toluene;
    transalkylating;
    separating para-xylene with a simulated moving bed para-xylene separation step; and
    isomerizing xylene;
    wherein,
    a resultant of the sulforan process is inputted to the benzene/toluene fractionation step,
    the toluene from the benzene/toluene fractionation step is inputted to the selective toluene disproportionation step and the transalkylation step,
    a resultant of the selective toluene disproportionation step is inputted again to the benzene/toluene fractionation step,
    resultants of the benzene/toluene fractionation step and the transalkylation step are inputted to the aromatic compound fractionation step,
    a xylene mixture from the aromatic compound fractionation step is inputted to the simulated moving bed para-xylene separation step, and
    the xylene mixture from the simulated moving bed para-xylene separation step is inputted to the xylene isomerization step, and wherein,
    the method further comprises a simulated moving bed xylene mixture pre-treatment step and an additional xylene isomerization step, wherein the simulated moving bed xylene mixture pre-treatment step is applied between the aromatic compound fractionation step and the simulated moving bed para-xylene separation step, and the xylene mixture from the simulated moving bed xylene mixture pre-treatment step is inputted to the additional xylene isomerization step.

2. The method for separating aromatic compounds according to claim 1, wherein the xylene mixture pre-treatment step and the additional xylene isomerization step comprise the following steps:
    (1) inputting a part of the xylene mixture that is to be inputted to the simulated moving bed para-xylene separation step, to the simulated moving bed xylene mixture pre-treatment step;
    (2) inputting the xylene mixture containing 80% by weight or more para-xylene in the resulted product obtained from the simulated moving bed xylene mixture pre-treatment step, to the simulated moving bed para-xylene separation step, and the remaining portion of the xylene mixture is inputted to the additional xylene isomerization step;
    (3) re-inputting the resulted product obtained from the additional xylene isomerization step to the aromatic compound fractionation step.

3. The method for separating aromatic compounds according to claim 2, wherein a portion of the resulted products from the additional xylene isomerization step which are to be inputted to the the aromatic compound fractionation step (3), is inputted to the benzene/toluene fractionation step.

4. The method for separating aromatic compounds according to claim 1, wherein the toluene is additionally supplied to the selective toluene disproportionation step.

5. The method for separating aromatic compounds according to claim 1, wherein the xylene mixture is additionally supplied to the aromatic compound fractionation step.

6. The method for separating aromatic compounds according to claim 2, wherein the toluene is additionally supplied to the selective toluene disproportionation step.

7. The method for separating aromatic compounds according to claim 3, wherein the toluene is additionally supplied to the selective disproportionation toluene step.

8. The method for separating aromatic compounds according to claim 2, wherein the xylene mixture is additionally supplied to the aromatic compound fractionation step.

9. The method for separating aromatic compounds according to claim 3, wherein the xylene mixture is additionally supplied to the aromatic compound fractionation step.

* * * * *

UNITED STATES PATENT AND TRADEMARK OFFICE
CERTIFICATE OF CORRECTION

PATENT NO.       : 8,431,763 B2  
APPLICATION NO.  : 12/532751  
DATED            : April 30, 2013  
INVENTOR(S)      : Lee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 406 days.

Signed and Sealed this
Eighth Day of September, 2015

Michelle K. Lee
*Director of the United States Patent and Trademark Office*